United States Patent [19]

Stein

[11] 4,216,233
[45] Aug. 5, 1980

[54] METHOD FOR TREATMENT OF SKIN BURNS IN MAMMALS

[76] Inventor: Karl N. Stein, 4137 Regal Oak Dr., Encino, Calif. 91346

[21] Appl. No.: 966,968

[22] Filed: Dec. 6, 1978

[51] Int. Cl.² .............................................. A61K 31/02
[52] U.S. Cl. ............................ 424/350; 424/DIG. 13
[58] Field of Search ................ 424/350; 426/DIG. 13

[56] References Cited

U.S. PATENT DOCUMENTS 2,801,201   7/1957   Kipnis ...................... 424/DIG. 13 X

OTHER PUBLICATIONS

Travell et al.-J. of Pharmacology & Experimental Therapeutics, 1951, vol. 101, p. 36.
Lautsevichos-Kunicheskaya Meditsina, Moscow, vol. 53, No. 5, pp. 55–57.

*Primary Examiner*—Leonard Schenkman
*Attorney, Agent, or Firm*—Hubbell, Cohen, Stiefel & Gross

[57] ABSTRACT

A method for treating skin burns in mammals where hot, molten organic substances have been deposited on, and are adhering to and aggravating, burned skin areas includes quickly but gently applying sufficient volatile cooling solvent to the affected areas to remove such adhering substances from these areas without further substantial injury thereto, while cooling the areas.

6 Claims, No Drawings

METHOD FOR TREATMENT OF SKIN BURNS IN MAMMALS

This invention relates to a method for the treatment of skin burns in mammals. More particularly, the invention relates to a method for therapeutically treating such burns where hot, molten organic substances such as tars, asphalts, bitumens and pitches have been deposited on, and are adhering to and aggravating, these burns. The new method comprises rapidly but gently applying sufficient volatile cooling solvent to the affected areas to soften the adhering substances, or to dissolve them, to remove them from these areas with minimum abrasion thereof.

The volatile cooling solvents deposit sufficient liquid on the adhering substances to remove them with minimum abrasion, but vaporize rapidly to cool the affected area. Preferably, these solvents are applied in the form of a spray. As used herein, the term "spray" includes sprays, aerosols, and other finely divided particulate delivery forms. These application techniques minimize aggravation of the affected areas, facilitate rapid, gentle application to those areas, and lead to efficient use of the solvents. Treatment should begin as promptly as possible after burns occur, preferably within one or two hours thereafter.

Suitable volatile cooling solvents must have physical properties adequate to assure that at least a portion of the solvent remains on the affected areas in liquid form for a time sufficient to dissolve or soften and to remove the adhering substances. They must also have sufficient power to dissolve and remove the adhering substances from these areas, or at least to soften them sufficiently to remove them, in both cases without further substantial injury to the affected area. Solvating action of such solvents on such substances should not produce heat. Rather, such solvents should vaporize readily to cool the burned skin areas while solvating or softening the adhering substance. Of course, these solvents should not have substantial harmful side effects, and should be non-flammable at standard temperature and pressure. More specifically, the cooling solvents should not be substantial skin irritants or skin sensitizers.

The volatile cooling solvents are liquids at standard temperature and pressure, and may be chosen from any of several substances, depending on the nature and especially the solubility of the hot, molten substances adhering to the affected areas to be treated. Upon application to the affected area, the volatile cooling solvents partially vaporize, with the heat of vaporization coming from the adhering substances, thus cooling the affected areas. Simultaneously, the deposited liquid on the affected area softens or dissolves the adhering substances and allows them to be removed without further substantial injury to the affected areas. To function in these ways, the volatile cooling solvents should have boiling points below 50° C., preferably below about 30° C., to facilitate vaporization, but above 0° C. so as to deposit liquid on the affected area without flashing of the solvent or freezing of the skin.

Among the volatile cooling solvents useful alone in the new method are various acyclic aliphatic hydrocarbons and ethers, such as n-pentane, isopentane, methylethyl ether and diethyl ether. Especially preferred are the halogenated, short chain (particularly those having 1 and 2 carbon atoms) aliphatic acyclic hydrocarbons containing at least one atom of fluorine, bromine or chlorine. These halocarbons have sufficient solvating power to soften or dissolve a broad spectrum of hot, molten organic substances, and are less flammable than the corresponding hydrocarbon or ether solvents. Indeed, where fully substituted with halogens, such halocarbons are non-flammable. Examples of such halocarbons are ethyl chloride, methyl bromide, methylene chloride, dichloromonofluoromethane, 1,2-dichloro-1,2-difluoroethane, 1-dichloro-1-monofluoro-2-trifluoroethane, and 1-monochloro-2-trifluoroethane.

Mixtures of these halocarbons also work well. For example, a mixture of dichlorodifluoromethane and trichloromonofluoromethane has been used effectively in treating one burn victim who had hot, molten tar adhering to his skin.

In one preferred embodiment of this invention, ethyl chloride is highly effective in removing hot, molten bitumens, tars, asphalts and pitches adhering to and aggravating skin burns, particularly when rapidly applied as a spray within an hour or two after the burn has occurred.

Alternatively, the volatile cooling solvents may be a mixture of substances. This permits using one or more constituents that have boiling points outside the ranges set forth above. Thus, hydrocarbons such as the butanes and ethers such as dimethyl ether boiling below 0° C. at STP, alcohols such as methyl alcohol and ethyl alcohol, and ketones such as acetone, all boiling above 50° C. at STP, may be combined with other solvents to form mixtures that have the requisite boiling point characteristics. This permits using solvents that may be better suited to softening or dissolving certain kinds of organic substances than are those solvents that can be used alone.

Among the organic substances that may cause burns when they splash onto or otherwise contact skin in hot, molten or plastic condition are: fats, waxes, adhesives, glues, plastics, resins, soaps, detergents, asphalts, tars, bitumens, pitches, oils and other organic chemicals. As used herein, the phrase "hot, molten, organic substances" includes all these substances and their solidified forms. Such substances may contain combined sulfur, oxygen and/or nitrogen, which may adversely affect skin burns even after cooling. By removing these from the affected areas, the new method minimizes such effects.

In a preferred embodiment of this invention, skin burns caused by and aggravated by asphalts, tars, pitches and bitumens are treated in accordance with the new method. Because these organic substances are amorphous and adhere tenaciously to skin, they aggravate both the severity and pain of burns they cause. The new method effectively removes them, minimizing the burn pain and severity, especially when treatment takes place promptly after the burn occurs.

The new method performs well at standard pressures and temperatures. In practice, no dangerous or difficult operating conditions affect the process, and the process works far more rapidly, completely, therapeutically, and with less pain to remove the adhering substances and to promote healing without scarring than does the present clinical treatment of such burns. The treatment commonly used today involves rapid chilling of the burned area, which solidifies the material adhering to the skin but does not soften or dissolve it. This makes it difficult to cool rapidly the surface that is next to the skin. The solidified material continues to aggravate the burn, increasing the likelihood of scarring and deformity. Skin grafts or other surgery is often necessary to repair these areas. Although mineral oils have been used to dissolve such adhering substances, their solvent action is far too slow to prevent scarring, and such oils do not cool the burns. Further, prior art techniques invariably require mechanical removal of the adhering substances, thus abrading the burned skin areas, increasing further the likelihood of scarring. The method of this invention eliminates the need for mechanical removal of the adhering substances, reducing materially the likelihood of scarring.

In clinical tests, the new process has worked extremely well. As one example, a middle-aged man spilled a barrel of hot, molten tar over himself, creating burns over 28% of his body. The hot tar solidified and adhered to his face, neck, chest, arms and hands, causing severe pain. One half hour after the spill, all available ethyl chloride was sprayed directly onto the coated and burned skin areas to dissolve the tar on this patient in the following order: First, his hands, then his face, his neck, and finally his joint areas such as the elbows, shoulders and wrists. There was insufficient ethyl chloride to treat his chest and the rest of the burned areas on his arms. After he stabilized, he was transferred to the burn center for conventional treatment.

Clinical examination of this patient two months after he was first burned revealed that the areas treated with ethyl chloride had healed with virtually no scarring. On his neck, where a small piece of tar had been mechanically removed with his clothes, there was a small scar. His hands were, and remain, fully functional and unscarred. Untreated areas on his arms and chest resulted in third degree burns, and required skin grafts. Two months after this patient's face, neck, chest, hands and arms had been severely burned, he returned to work full time with no significant limitation, primarily because of the new method's effectiveness.

What is claimed is:

1. A method for treating a skin burn aggravated by a hot, molten organic substance selected from the group consisting of tars, asphalts, bitumens and pitches adhering thereto, which comprises applying to the affected area a cooling solvent consisting essentially of a halogenated, short chain aliphatic acyclic hydrocarbon substituted by at least one atom of fluorine, bromine or chlorine, and having a boiling point of from 0° to 50° C. or mixtures thereof, to soften or dissolve and remove the organic substance while cooling the affected area without further injury to the burned skin.

2. The method of claim 1 wherein the cooling solvent is ethyl chloride.

3. The method of claim 1 wherein the cooling solvent is a mixture of at least two of said hydrocarbons.

4. A method for treating a skin burn aggravated by a hot, molten organic substance selected from the group consisting of tars, asphalts, bitumens and pitches adhering thereto, which comprises spraying the affected area with a volatile cooling solvent consisting essentially of a halogenated, short chain aliphatic acyclic hydrocarbon substituted by at least one atom of fluorine, bromine or chlorine, and having a boiling point of from 0° to 50° C. of mixtures thereof, to cool the burned skin and to soften or dissolve and remove the adhering substance without further substantial injury to the burned skin, and without substantial mechanical manipulation of the adhering substance.

5. The method of claim 4 wherein the cooling solvent is ethyl chloride.

6. The method of claim 4 wherein the cooling solvent is a mixture of at least two of said hydrocarbons.

* * * * *